United States Patent [19]

DeMeo et al.

[11] Patent Number: 4,798,580
[45] Date of Patent: Jan. 17, 1989

[54] DISPOSABLE PERISTALTIC PUMP CASSETTE SYSTEM

[75] Inventors: Deborah A. DeMeo, Hatboro; Robert M. Bross, Ivyland; Kenneth P. Cook, Blue Bell, all of Pa.

[73] Assignee: Site Microsurgical Systems, Inc., Horsham, Pa.

[21] Appl. No.: 43,120

[22] Filed: Apr. 27, 1987

[51] Int. Cl.[4] ............................................. A61M 1/00
[52] U.S. Cl. ...................................... 604/30; 604/34; 604/35; 604/119; 604/153; 417/476
[58] Field of Search ..................... 604/22, 27, 30, 31, 604/32, 33, 34, 35, 153, 155, 118–120, 317; 417/475, 476, 477, 360

[56] References Cited

U.S. PATENT DOCUMENTS

| | | | |
|---|---|---|---|
| 3,723,030 | 3/1973 | Gelfand | 417/477 |
| 3,841,799 | 10/1974 | Spinosa et al. | 417/477 |
| 4,168,707 | 9/1979 | Douvas et al. | 604/35 |
| 4,187,057 | 2/1980 | Xanthopoulos | 417/63 |
| 4,256,437 | 3/1981 | Brown | 417/45 |
| 4,256,442 | 3/1981 | Lamadrid et al. | 417/475 |
| 4,424,011 | 1/1984 | O'Brien et al. | 417/477 |
| 4,445,826 | 5/1984 | Tarr | 417/476 |
| 4,482,347 | 11/1984 | Borsanyi | 604/153 |
| 4,493,695 | 1/1985 | Cook | 604/27 |
| 4,515,589 | 5/1985 | Austin et al. | 604/122 |
| 4,526,515 | 7/1985 | DeVries | 417/63 |
| 4,537,561 | 8/1985 | Xanthopoulos | 417/63 |
| 4,599,055 | 7/1986 | Dykstra | 417/477 |
| 4,627,833 | 12/1986 | Cook | 604/34 |
| 4,685,902 | 8/1987 | Edwards et al. | 604/153 |
| 4,713,051 | 12/1987 | Steppe et al. | 604/30 |
| 4,714,464 | 12/1987 | Newton | 604/30 |
| 4,735,558 | 4/1988 | Kienholz et al. | 417/477 |

FOREIGN PATENT DOCUMENTS

| | | | |
|---|---|---|---|
| WO86/07249 | 12/1986 | PCT Int'l Appl. | 604/22 |
| 2176717 | 1/1987 | United Kingdom | 604/317 |

Primary Examiner—C. Fred Rosenbaum
Assistant Examiner—Mario Costantino
Attorney, Agent, or Firm—W. Brinton Yorks, Jr.

[57] ABSTRACT

A microsurgical irrigation/aspiration system is provided, including a controller having a pump roller head, actuators for occluding tubing, a suction sensor, and apparatus for mounting a pump cassette. The system cassette is suitable for mounting on the controller and has an opening with a pump tubing segment passing along an arcuate wall of the opening. When the cassette is mounted on the console, the roller head is engaged in the cassette opening and compresses the pump tubing segment against the arcuate wall. An infusion line passes through the cassette and is occludable by one of the actuators, and a vent line connected to the pump tubing segment is occludable by a second actuator. A suction sensing port on the cassette couples with the suction sensor in the controller.

18 Claims, 4 Drawing Sheets

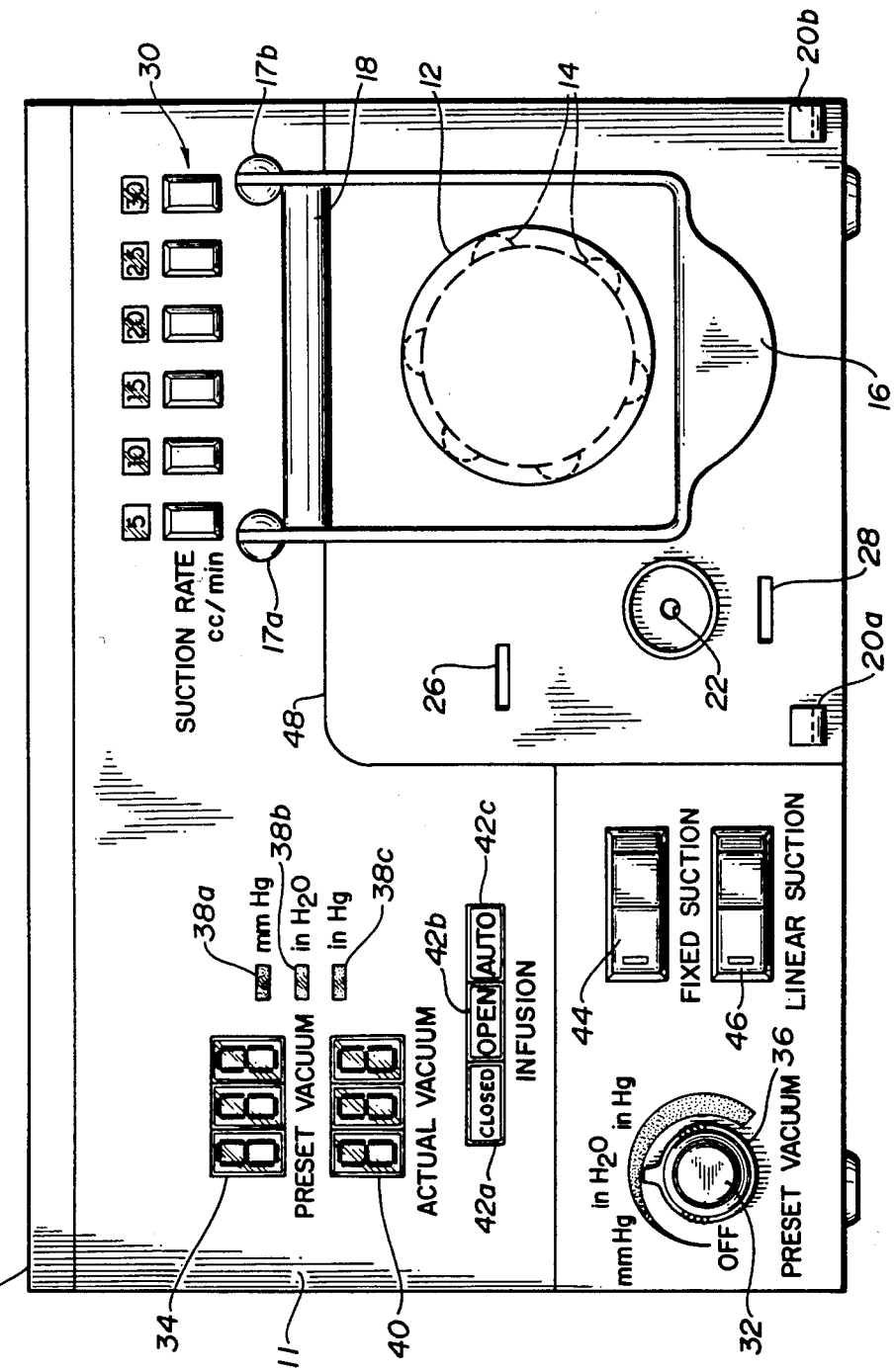

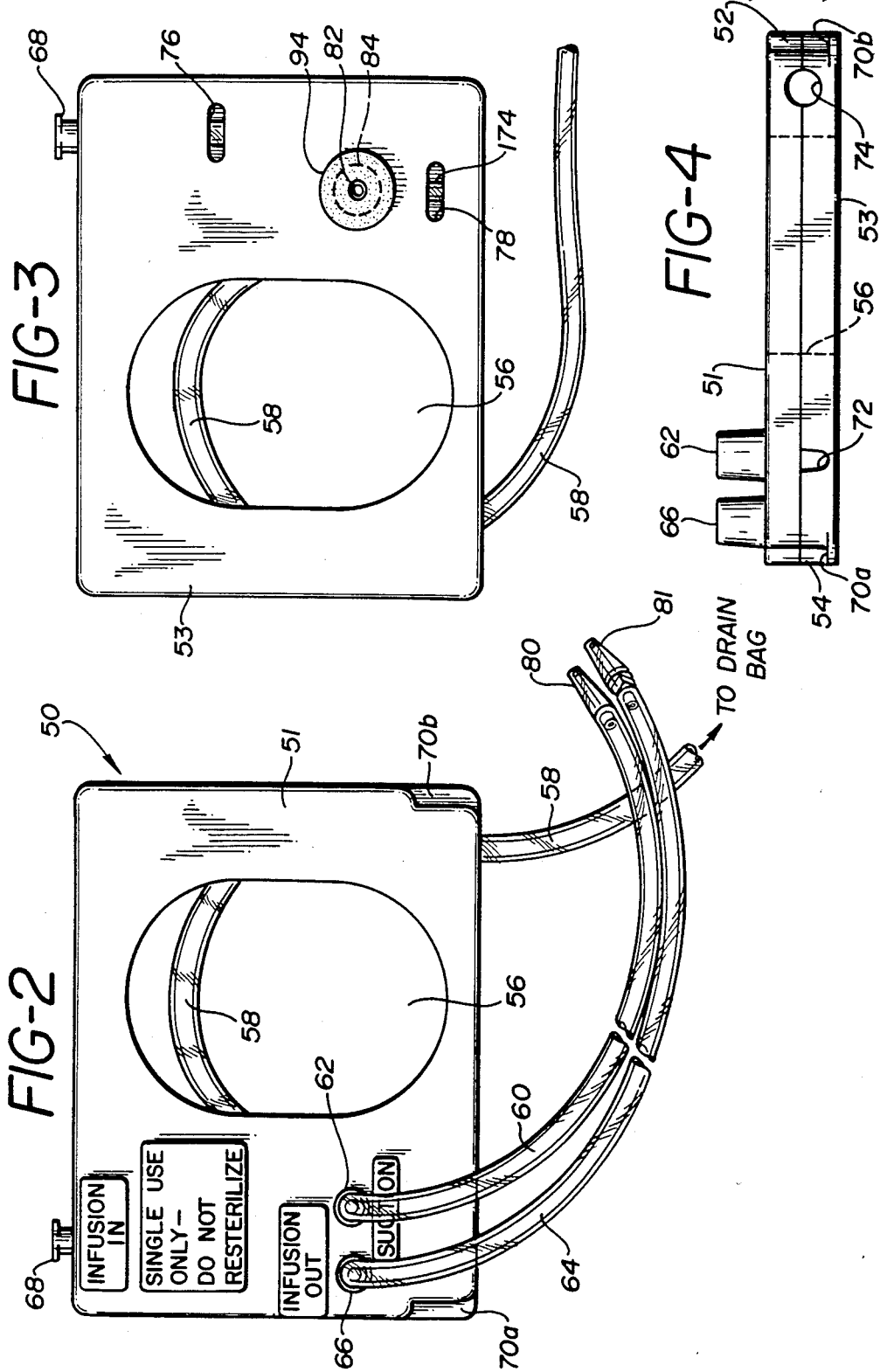

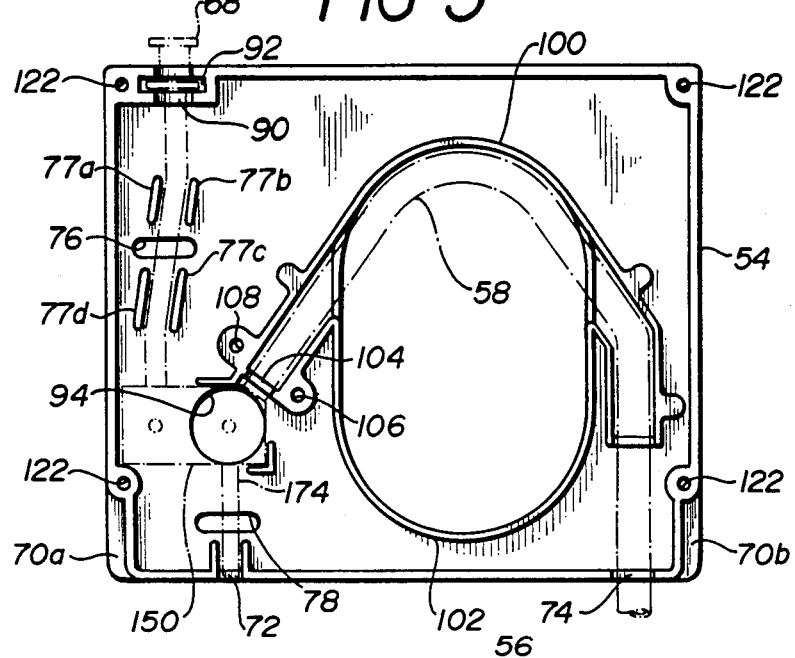
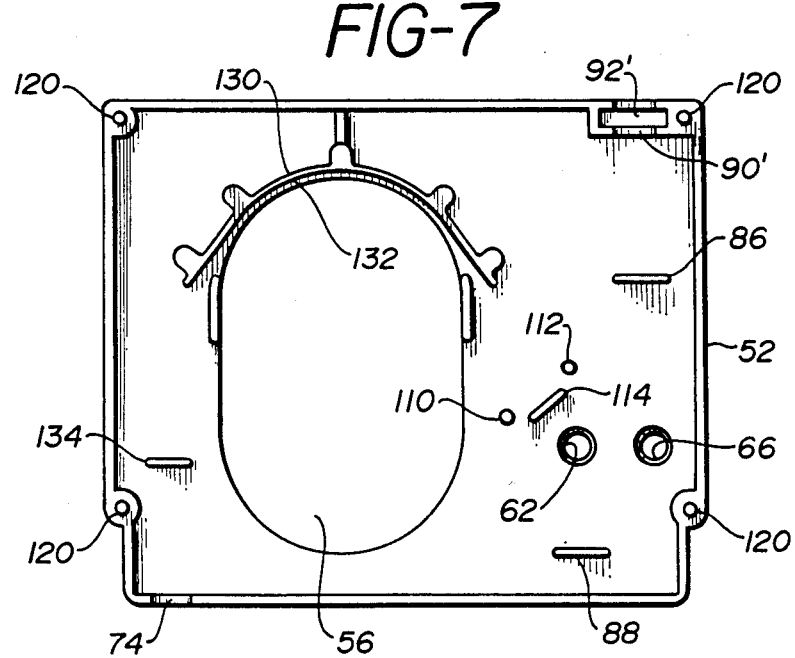

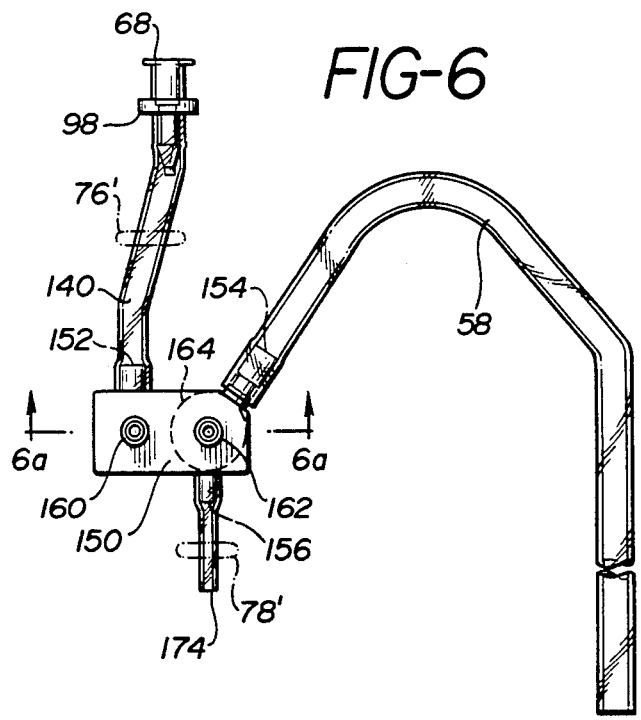
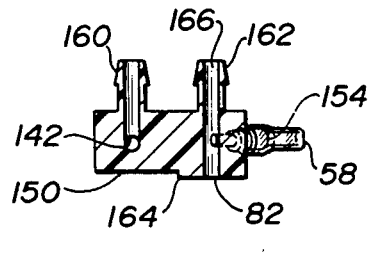
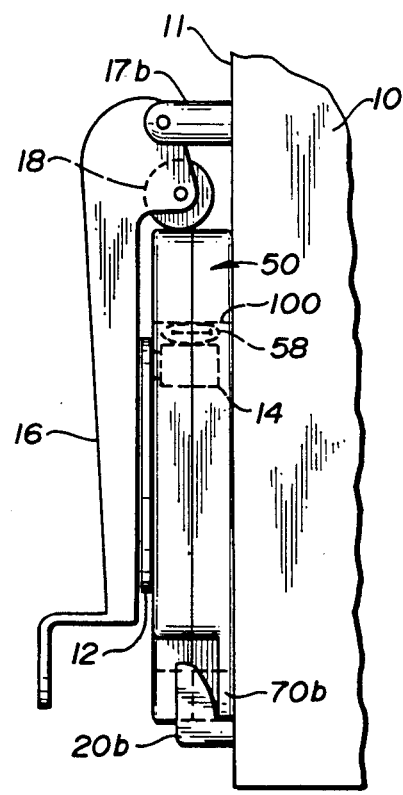

DISPOSABLE PERISTALTIC PUMP CASSETTE SYSTEM

This invention relates to peristaltic pumps and, in particular, to peristaltic pump systems with disposable cassettes adaptable for use in ophthalmic microsurgery.

In ophthalmic microsurgery, commonly employed surgical instruments such as electro-mechanical or pneumatically driven cutters and phacoemulsification instruments require a source of liquid to infuse a surgical site, and a source of negative pressure to evacuate the infusion liquid and debris from the site. Systems which perform these liquid flow functions for microsurgical instruments are commercially available, and are known as infusion/aspiration systems. One such system which has gained widespread acceptance is the SITE TXR* system, the fundamental principles of which are described in U.S. Pat. No. 4,493,695. That patent describes a cassette assembly which mounts on a modular control console. The control console interfaces with the cassette to provide a source of vacuum for a suction line connected between the cassette and the surgical instrument, and control means for controlling the application of suction and infusion fluid for the instrument. Connected to the cassette and in fluid communication with the suction line is a collection bottle which collects the aspirated liquid and debris from the surgical site. For each surgical procedure a new cassette and collection bottle are mounted on the console and the cassette and bottle are disposed of after the procedure, thereby insuring that a completely sterile fluid system is used for each procedure.

The console of the patented system includes a diaphragm vacuum pump which provides the source of suction for the cassette. Another mechanism which is capable of supplying fluid pressure for medical apparatus is the peristaltic Pump, which is desirable for its ability to provide liquid suction. A peristaltic pump generally includes a motor driven head containing a number of rollers. A section of collapsible tubing is securely mounted around the roller head by a clamping mechanism. As the roller head turns, individual rollers sequentially compress the tubing and squeeze liquid through it in the direction of rotation of the roller head.

Peristaltic pumping systems are often preferred over diaphragm pumps by physicians due to their more gentle application of suction. When a diaphragm pump is activated during surgery, it provides a sudden increase in vacuum pressure at the surgical site. The sudden vacuum pressure can cause the held-held surgical instrument to immediately "grab" onto nearby tissue. The vacuum pressure can cause tissue material to be drawn to the instrument, and the "grabbing" action can unintentionally damage nearby tissue. The peristaltic pump will provide a gradual increase in vacuum pressure as the roller head starts to rotate. So long as the peristaltic pump is only drawing liquid into the instrument, there will be only a very slight negative pressure at the tip of the instrument. Tissue does not move to the instrument; rather, the instrument must be moved to the tissue before the low suction level begins to grab onto tissue. When the suction port grabs onto tissue, a partial or total occlusion will occur. At that time the suction in the line will build until the tissue is drawn away from the surgical site and removed.

When a peristaltic pump is used in an infusion/aspiration system, the previously described need for sterility of the fluid system is still present. It is desirable for a disposable system for the peristaltic pump to provide all of the fluid control required in an infusion/aspiration system. The disposable system should be economical to produce so it can be disposed of after use without incurring a large expense. The disposable system should also be compact so as to require a minimal storage area in a hospital or other medical facility.

In accordance with the principles of the present invention a peristaltic pumping system for infusion/aspiration procedures is provided which includes a disposable pump cassette. The system includes a console with a roller head, means for mounting the cassette over the roller head, and interrupter bars for occluding tubing in the cassette. An infusion fluid line passes through the cassette, and is aligned with an interrupter bar in the console. The interrupter bar is selectably controlled to control the flow of infusion liquid to the surgical site. A suction line is connected to the cassette and is curved around an arcuate opening in the cassette which is located around the roller head. Rotation of the roller head will thereby draw liquid from the surgical site through the suction line.

In a preferred embodiment of the present invention, a Pressure sensing port is connected to the suction line of the cassette. The pressure sensing port connects to a pressure sensor within the console, which monitors the suction pressure. A constructed embodiment of the cassette of the present invention is very compact, measuring about 3.5 inches by 4 inches by one-half inch thick, and is economical to manufacture and assemble.

In the drawings:

FIG. 1 illustrates a peristaltic pump module constructed in accordance with the principles of the present invention;

FIG. 2 is a front plan view of a peristaltic pump cassette suitable for us with the module of FIG. 1;

FIG. 3 is a rear plan view of the cassette of FIG. 2;

FIG. 4 is a bottom plan view of the cassette of FIG. 1;

FIG. 5 is an internal view of the back half of the cassette of FIG. 2;

FIG. 6 is a view of the junction block and associated tubing segments shown in FIG. 5;

FIG. 6a is a cross-sectional view taken along line 6a-6a of FIG. 6;

FIG. 7 is an internal view of the front half of the cassette of FIG. 2; and

FIG. 8 is a side view of the cassette of FIGS. 2-7 when mounted on the module of FIG. 1.

Referring to FIG. 1, a peristaltic pump module 10 constructed in accordance with the principles of the present invention is shown. A constructed embodiment of this module has been built as a modular add-on to the SITE TXR* system. This mainframe system includes a chassis which can accommodate a number of modules that perform different functions for the ophthalmic surgeon, including the control of surgical cutting instruments and infusion and aspiration. The module shown in FIG. 1 is representative of one of these modules which provides infusion and peristaltic pump aspiration.

On the front panel 11 of the module are a number of controls and displays. A concentric switch includes a center knob 32 which turns the module on and is adjustable to set the maximum suction level to be applied by the peristaltic pump. As the knob 32 is adjusted the numbers displayed by the preset vacuum display 34 will vary to indicate the setting of the maximum vacuum.

The outer knob 36 is adjustable to one of three settings: mm Hg, in. H₂O, and in. Hg. The setting of knob 36 illuminates one of three corresponding lights 38a, 38b, or 38c, which inform the user as to the units in which the vacuum measurements are being displayed by displays 34 and 40. The display 40 constantly displays the vacuum level at the inlet (suction) line to the peristaltic pump. A pressure sensor accesses the suction line through a port 22.

Three pushbuttons 42a, 42b, and 42c provide control of the liquid infusion line. When the "auto" pushbutton 42c is depressed, the infusion line is opened automatically whenever a control pedal (not shown) is depressed to start the pump, and is automatically occluded by the extension of a solenoid actuated interrupter bar through opening 26 when the control pedal is released. The other two pushbuttons provide manual control of the infusion line. When "closed" pushbutton 42a is depressed, the interrupter bar extends to occlude the infusion line, and when "open" pushbutton 42b is depressed the interrupter bar retracts to open the line. The control functions of pushbuttons 42a and 42b operate independently of the control pedal.

The pump speed, and hence the rate at which the vacuum level is developed by the pump, is set by depressing one of pushbuttons 30. Each pushbutton controls the suction rate, as measured in cubic centimeters of flow per minute through an unblocked suction line. Two types of suction control are available. When the "fixed suction" switch 44 is set, the pump will immediately begin pumping at the preset suction rate when the control pedal is depressed. When the "linear suction" switch 46 is set, the operator can accelerate the suction rate up to the preset rate by controllably depressing the control pedal.

The pump mechanism includes a brushless DC motor and gearbox located within the module which rotates a pump head 12. Evenly spaced around the pump head are six rollers 14. The pump head is turned in a clockwise direction by the motor so that the rollers will sequentially and smoothly squeeze the pump tubing as they pass along the upper quadrant of the pump head location.

The pump cassette, to be described below, is affixed in an area outlined by 48. The cassette is supported at the bottom by the placement of tabs at the bottom corners of the cassette in two retaining brackets 20a and 20b. The cassette is held in place by a cam bar 18 at the top of the cassette. The cam bar is secured between the sides of a latch 16, which is pivotally connected to latch supports 17a and 17b above the area 48. When the cassette is placed in position with its tabs located in the brackets 20a and 20b, the latch may be swung down so that the cam bar engages the upper edge of the cassette. The latch is then pressed firmly against the front surface of the cassette, causing the cam bar to roll to the center of the cassette top which presses the suction tubing of the cassette against the pump head. The cam bar distributes pressure equally across the top of the mounted cassette.

A second solenoid actuated interrupter bar controllably extends through opening 28 in the front panel to selectively open or occlude a vent line to the suction line of the cassette.

Referring to FIGS. 2-4, views of the outside of a cassette 50 suitable for use with the module 10 are shown. FIG. 2 illustrates the front surface 51 of the cassette. The cassette is characterized by an oval opening 56 which accommodates the pump head. The width and arc of the opening 56 are sized to be just slightly larger than the pump head.

Located at the top of the cassette is an inlet luer 68 of the infusion line. The infusion line exits the cassette through tubing 64. The tubing 64 is connected to a barbed fitting within the cassette. This connection is protected by a molded guard 66 which projects from the front 51 of the cassette. The guard 66 is also shown in FIG. 4. The infusion tubing 64 terminates in a luer 81, by which the tubing may be connected to the infusion port of an infusion/aspiration handpiece or a surgical cutting instrument.

A suction tubing line 60 has a molded adapter piece 80 connected at its free end for connection to the suction, or aspiration, port of the handpiece or instrument. Tubing 60 is similarly connected to a barbed fitting within the cassette which is protected by a molded guard 62. The suction line passes through the cassette and makes a transition to a pump tubing segment 58. The tubing segment 58 enters the opening 56 through an aperture in the interior wall of the opening, passes along the inside wall along its upper arc, and exits the opening through an aperture in the interior wall on the opposite end of the arc from which it entered. The tubing segment is made of a material suitable for use in a peristaltic pump, such as silicone. In a constructed embodiment, this tubing segment has a ⅛ inch inner diameter and a ¼ inch outer diameter.

The tubing segment 58 exits the cassette through a hole in the bottom, from which it leads to a means for disposing of aspirated material such as a drain bag.

Along each vertical side of the cassette 50, the body of the cassette is thinned to form corner tabs 70a and 70b. These corner tabs fit snugly into the retaining brackets 20a and 20b of the module 10.

FIG. 3 shows the back surface 53 of the cassette 50, including the previously described infusion line inlet luer 68, the opening 56, and pump tubing segment 58. Also shown are an aperture 76 through which the interrupter bar of opening 26 enters the cassette, and an aperture 78 for passage of the interrupter bar of opening 28. A vent line tubing segment is visible through aperture 78, and an infusion line tubing segment is visible through aperture 76. There is a hole 94 through the back of the cassette for passage of a pressure sensing port 82, which mates with the port 22 when the cassette is mounted on the module 10. The port 82 is surrounded by a foam sealing gasket 84.

FIG. 4 is a bottom view of the cassette 50, which is seen to be comprised of a front half 52 and a back half 54. Guards 66 and 62 which extend from the front surface 51 are shown at the top of the drawing. Aperture 74 is provided for passage of tubing segment 58, which for clarity is not represented in FIG. 4. Aperture 72 is an opening for the vent line. On either side of the cassette bottom the corner tabs 70a and 70b may be seen.

Referring to FIG. 5, the interior of the back cassette half 54 is shown, with tubing segments and a junction block 150 drawn in phantom for ease of illustration. The infusion luer 68 enters the top of the cassette through a semicircular aperture in a block 90. The block 90 includes a rectangular opening 92 which retains a collar of the luer 68 to hold the luer in place. An infusion line tubing segment 140 extends from the luer 68 to the junction block 150. The tubing segment 140 passes over the interrupter bar aperture 76, and is maintained in this position by four molded guides 77a-77d. Vent tubing segment 174 extends from the junction block 150 to the aperture 72 and passes over the interrupter bar aperture 78.

The pump tubing segment 58 is retained in its intended position by a molded upper guide 100 and the opposite ends of a molded lower guide 102. A curved, molded protrusion 104 spans the two guides proximate the junction block 150 to serve as a portion of an integral clamp which secures the tubing segment 58 on its junction block fitting. A molded bracket with holes 106 and 108 at the ends of the location of protrusion 104 mates with pins in the front cassette half to secure the integral tubing clamp.

A portion of the upper guide 100 is seen to be contiguous with the upper arc of the opening 56. This portion of the guide serves two further purposes: it forms the upper interior wall of the opening 56, and it is the surface against which the tubing segment 58 is compressed by the pump head. The central portion of the lower guide 102 similarly is contiguous with the perimeter of the opening 56, and likewise forms the side and lower arcuate interior walls of the opening. It may be seen that the spaces between the two guides at their intersections with the opening perimeter form the apertures through which the pump tubing segment 58 enters and exits the opening 56.

Located at the upper two corners of the back cassette half 54 and just above each of the tabs 70a and 70b are holes 122 which mate with pins of the front cassette half 52.

FIG. 7 shows the interior of the front cassette half 52. A block 90' with an opening 92' mates with block 90 of the back cassette half to capture the luer 68 and its collar. A protrusion 86 forms an anvil surface for occluding tubing segment 140. The interrupter bar entering the cassette through aperture 76 will squeeze and thereby occlude the infusion line tubing segment 140 between the interrupter bar and the protrusion 86. Below the protrusion 86 are two holes through which the molded guards 62 and 66 on the front surface of the cassette may be seen. Below the hole surrounded by guard 62 for the suction line is a protrusion forming an anvil surface 88. The interrupter bar entering aperture 78 occludes the vent tubing segment 174 between the protrusion 88 and the interrupter bar.

Curved protrusion 114 extends to form the second half of the integral clamp which secures tubing segment 58 on its junction block fitting when the two cassette halves are mated together. Pins 110 and 112 fit into holes 106 and 108 of the molded bracket in the back cassette half to secure the integral clamp for the pump tubing segment. A protrusion 134 fits between the ends of the guides 100 and 102 where the tubing segment 58 leaves the two guides.

Located around the upper arc of the opening 56 is a reinforced support wall 130. The support wall 130 is spaced slightly above the perimeter of the opening so that the upper guide 100 of the back cassette half will fit flush against surface 132 of the support wall. The support wall thus supports the upper arcuate portion of the guide 100 where it opposes the compressive forces of the pump head rollers as the tubing segment 58 is compressed.

Located at the upper corners of the front cassette half and just above the tab locations are pins 120, which mate with the holes 122 in the back cassette half. It may be seen that when the two cassette halves are mated together, they are fastened to each other by the four pins 120, pins 110 and 112, and their respective holes.

FIG. 6 illustrates the cassette tubing segments and junction block which were shown in phantom in FIG. 5, and in the same configuration. FIG. 6 clearly shows the collar 98 of the infusion line female luer 68 which fits into the rectangular openings 92, 92' of the cassette halves. The phantom lines 76' indicate the location of aperture 76 behind the infusion line tubing segment 140 in an assembled cassette. The infusion line tubing segment 140 is connected to a luer 152 on the junction block 150, and the vent tubing segment 174 is connected to a luer 156 on the junction block. The location of aperture 78 relative to the vent tubing segment in an assembled cassette is indicated by phantom lines 78'.

The pump tubing segment 58 is connected to a fitting 154 on the junction block. The fitting 154 has a narrow diameter neck, about which the integral clamp of the cassette secures the tubing segment to the fitting 154. Barbed fittings 160 and 162 extend normal to the plane of the drawing for connection to infusion tubing 64 and suction tubing 60. The fittings 160 and 162 are more clearly shown in FIG. 6a, which is a cross-sectional view of the junction block 150.

In FIG. 6a, the fluid passageways through the junction block 150 can be seen. A passageway 142 for the infusion line enters the junction block through fitting 152 on the back of the block as it is oriented in FIG. 6a, and continues through the barbed fitting 160. A suction line passageway 166 passes through the barbed fitting 162 and continues through the fitting 154. The extension of passageway 166 to the bottom of the junction block in FIG. 6a forms the pressure sensing port 82. The pressure sensing port 82 is surrounded by a raised mounting surface 164 for the sealing gasket 84 of FIG. 3. The diameter of surface 164, shown in phantom in FIG. 6, is sized to just fit into the hole 94 in the back half of the cassette (FIGS. 3 and 5).

FIG. 8 illustrates a side view of the cassette 50 when mounted for operation on the module 10. The mounted cassette is supported at the bottom by the placement of the corner tabs 70a and 70b in the retaining brackets 20a and 20b. This placement locates the cassette in its correct horizontal position on the module so that the cassette can be positioned with its back surface 53 flush against the front panel 11 of the module. In this position the pump head 12 extends through opening 56. The cassette is slightly raised from its final vertical alignment, as the tubing segment 58 is resting uncompressed between the pump head 12 and the guide wall 100.

To lower the cassette to its intended vertical alignment with the module, the latch 16 is pivoted downward over the cassette. This causes the cam bar 18 to first contact the upper front edge of the cassette, then to forcibly roll on to the top of the cassette, as shown in FIG. 8. The cam bar 18 thus presses the cassette downward with the corner tabs 70a and 70b firmly seated in the retaining brackets, and at the same time compresses tubing segment 58 between the guide wall 100 and the rollers 14 of the pump head 12. The interrupter bar apertures 26 and 28 of the module are then aligned with their corresponding apertures 76 and 78 on the back of the cassette. The pressure sensing ports 22 and 82 are likewise aligned.

The pump cassette system is now ready for operation. Referring to FIG. 1, the user sets the preset vacuum level with the knob 32 and its units of display with the knob 36. The suction rate is set by pressing one of pushbuttons 30, and the mode of suction control is set by setting one of switches 44 and 46. The infusion line may be controlled automatically by depressing pushbutton 42c, or pushbutton 42a may be pressed to close the infusion line until it is needed.

The fluid lines are connected by connecting a source of infusion liquid to the female luer 68. Generally, this will be a bag or bottle of liquid suspended above the module. Luer 81 and adapter 80 of tubing lines 64 and 60 are connected to the infusion and suction ports of the handpiece or surgical instrument, and the system may then be primed with liquid.

In operation with automatic infusion line control, where the control pedal is depressed the infusion line interrupter bar retracts to open the infusion line tubing segment. This occlusion control technique is the same as that used by the interrupter bars described in U.S. Pat. No. 4,493,695. Infusion liquid then flows through tubing segment 140, the junction block passageway 142, the barbed luer 160, and into the infusion tubing 64. Further depression of the control pedal causes the pump head to begin rotating, either immediately at its selected rate when fixed suction is set, or at a controlled accelerating rate to the selected rate if linear suction is called for. Suction then begins to build in the suction tubing line 60, and is continuously monitored at the port 82 of the junction block by the module's internal pressure sensor. The pump head continues to rotate so long as the pump is freely pumping liquid. When the actual vacuum level reaches the preset vacuum level, as would occur if the suction port of the instrument or handpiece becomes fully occluded with particles of tissue, the pump head rotation stops until the actual vacuum level falls to a predetermined level, such as 80% of the preset maximum level. At this point the pump head resumes its rotation to aspirate the tissue particles through the suction tubing line and away from the surgical site. Thus, there is no buildup of substantial suction pressure at the handpiece or instrument tip until an occlusion of the suction line occurs. This prevents the application of undesired suction pressures to the patient at the surgical site, and eliminates any tendency of the hand-held instrument to "grab" tissue, as would happen if continual suction were applied. The physician thus is more easily able to precisely control the instrument during the surgical procedure.

When the depressed control pedal is released by the physician, the infusion tubing segment 140 is occluded and the interrupter bar extending through aperture 78 of the cassette is momentarily retracted, opening the vent tubing segment 174 and equalizing the suction line vacuum to atmospheric pressure. The handpiece or instrument can then be moved about the surgical site without exposing the patient to any residual vacuum pressures in the suction line. If desired, the pump head may be momentarily rotated counterclockwise by depressing a button adjacent to the control pedal to expel any blockage from the tip of the handpiece or surgical instrument.

What is claimed is:

1. A microsurgical irrigation/aspiration system, comprising:
   roller head means for performing peristaltic pumping and axially extending from the outermost panel of an irrigation/aspiration instrument, including a plurality of rollers located in a plane offset from and parallel to the plane of said outermost panel; and
   removable cassette means for retaining a tubing section which cooperates with said roller head means in the performance of peristaltic pumping, including said tubing section, said cassette means having an aperture passing therethrough for engaging said roller head means so that said cassette is located in said plane and the outer dimensions of said cassette completely radially surround said rollers of said roller head means with said tubing section located between said roller head means and an interior wall of said cassette defining said aperture; said cassette further including a selectable occludable infusion line passing therethrough.

2. The microsurgical irrigation/aspiration system of claim 1, wherein said aperture is larger than said roller head means to allow said cassette means to initially engage said roller head means without compressing said tubing section.

3. The microsurgical irrigation/aspiration system of claim 2, wherein said aperture is defined by two opposing straight walls connected at opposite ends by two arcuate walls.

4. The microsurgical irrigation/aspiration system of claim 2, further comprising mounting means extending from said outermost panel for securely engaging said roller head means in said aperture with said tubing section compressed between said roller head means and one of said arcuate interior walls.

5. A microsurgical irrigation/aspiration system, comprising:
   a control system having an outermost panel;
   roller head means, extending from said outermost panel, for performing peristaltic pumping; and
   a disposable pump cassette, suitable for mounting with its greatest planar surface on said outermost panel so as to engage said roller head means, and including a tubing section located between said roller head means and an arcuate surface of said cassette when said cassette engages said roller head means, said cassette further including a selectable occludable infusion line which passes therethrough.

6. The microsurgical irrigation/aspiration system of claim 5, wherein said outermost panel further includes means for securing said cassette on said outermost panel with said tubing section compressed between said roller head means and said arcuate surface.

7. The microsurgical irrigation/aspiration system of claim 6, wherein said outermost panel further includes means for selectively occluding said infusion line.

8. The microsurgical irrigation/aspiration system of claim 7, wherein said cassette further includes a suction sensing port and a vent tubing line in fluid communication with said tubing section, and
   wherein said outermost panel further includes means for selectively occluding said vent tubing line and means for connecting a sensor in fluid communication with said suction sensing port.

9. A microsurgical irrigation/aspiration system comprising:
   a console, including roller head means for performing peristaltic pumping, bracket means for engaging a pump tubing cassette, and latch means for applying a compressive force to a pump tubing cassette; and
   a pump tubing cassette, including an opening for engaging and completely surrounding said roller head means, a pump tubing section located in said opening and opposing an interior wall of said cassette, and tab means, located on first side of said cassette for engaging said bracket means, wherein said latch means applies a compressive force to a second side of said cassette opposite said first side to maintain the engagement of said tab means and said bracket means, and to compress said pump tubing section between said wall and said roller head means.

10. A microsurgical irrigation/aspiration system comprising:

a disposable cassette having an opening defined by a continuous interior wall for engaging and completely surrounding a roller head, a pump tubing section located in said opening and opposing said wall of said opening, tab means located on one side of said cassette for engaging bracket means for mounting said cassette on a roller head console, and an irrigation tubing segment extending through said cassette.

11. The irrigation/aspiration system of claim 10, wherein said disposable cassette further includes means for allowing selective occlusion of said irrigation tubing segment.

12. The irrigation/aspiration system of claim 11, wherein said disposable cassette further includes a vent tubing segment in fluid communication with said pump tubing section.

13. The irrigation/aspiration system of claim 12, wherein said disposable cassette further includes means for allowing selective occlusion of said vent tubing segment.

14. The irrigation/aspiration system of claim 13, wherein said disposable cassette further includes a suction measuring port in fluid communication with said pump tubing section.

15. The irrigation/aspiration system of claim 14, wherein said tab means comprises first and second tab located at opposite corners of one side of said cassette.

16. A microsurgical irrigation/aspiration system comprising:

a disposable cassette having a body exhibiting a thickness, and exhibiting major dimensions of an outer surface located in a plate defined by the height and width of said cassette body, an opening in said body for engaging a roller head, a pump tubing section extending through at least a portion of said opening and opposing a wall thereof, an irrigation tubing segment extending through said cassette with an occludable portion of said irrigation tubing segment opposing an aperture in said outer surface, and a suction measuring line in fluid communication with said pump tubing section and passing through a second aperture in said outer surface.

17. A microsurgical irrigation/aspiration system comprising:

a disposable cassette having a body exhibiting a thickness, and exhibiting major dimensions located in a plane defined by the height and width of said cassette body, an opening in said body for engaging a roller head, a pump tubing section extending through at least a portion of said opening and opposing a wall thereof, an irrigation tubing segment extending through said cassette with an occludable portion of said irrigation tubing segment located parallel to said plane, and a suction measuring line in fluid communication with said pump tubing section and having an opening to the line in a plane which is parallel to said plane of said cassette body;

wherein said cassette further includes a vent tubing segment in fluid communication with said pump tubing section with an occludable portion of said vent tubing section located parallel to said plane of said cassette body.

18. The microsurgical irrigation/aspiration system of claim 17, wherein said cassette body further includes a back surface which is parallel to said plane of said cassette body, said suction measuring line extends through said back surface, and said irrigation tubing segment and said vent tubing segment re occludable through apertures in said back surface.

* * * * *